(12) United States Patent
Prause et al.

(10) Patent No.: US 9,213,020 B2
(45) Date of Patent: Dec. 15, 2015

(54) COUPLING MEDIUM SUPPLY OF AN ULTRASONIC TEST DEVICE

(75) Inventors: Reinhard Prause, Hurth (DE); Christof Breidenbach, Hurth (DE)

(73) Assignee: GE SENSING & INSPECTION TECHNOLOGIES GMBH, Hurth (DE)

( * ) Notice: Subject to any disclaimer, the term of this patent is extended or adjusted under 35 U.S.C. 154(b) by 694 days.

(21) Appl. No.: 13/504,886

(22) PCT Filed: Oct. 4, 2010

(86) PCT No.: PCT/EP2010/064712
§ 371 (c)(1),
(2), (4) Date: Jul. 13, 2012

(87) PCT Pub. No.: WO2011/051081
PCT Pub. Date: May 5, 2011

(65) Prior Publication Data
US 2012/0279307 A1    Nov. 8, 2012

(30) Foreign Application Priority Data

Oct. 28, 2009 (DE) .......................... 10 2009 051 097

(51) Int. Cl.
*G01N 29/27* (2006.01)
*G01N 29/28* (2006.01)
*G01N 29/265* (2006.01)

(52) U.S. Cl.
CPC .............. *G01N 29/28* (2013.01); *G01N 29/265* (2013.01); *G01N 29/27* (2013.01)

(58) Field of Classification Search
CPC ...... G01N 29/265; G01N 29/27; G01N 29/28
USPC .................................. 73/629, 620, 622, 644
See application file for complete search history.

(56) References Cited

U.S. PATENT DOCUMENTS

| | | | | |
|---|---|---|---|---|
| 4,683,752 | A | * | 8/1987 | Bradshaw .................... 73/642 |
| 4,787,240 | A | * | 11/1988 | McShane .................... 73/290 V |
| 5,439,288 | A | * | 8/1995 | Hoffman et al. .............. 366/137 |
| 6,945,112 | B2 | * | 9/2005 | Prause ............................ 73/622 |

(Continued)

FOREIGN PATENT DOCUMENTS

| | | |
|---|---|---|
| CN | 101339163 A | 1/2009 |
| DE | 10118124 A1 | 10/2002 |

(Continued)

OTHER PUBLICATIONS

Unofficial English translation of a CN Office Action dated Feb. 20, 2014 issued in connection with corresponding CN Application No. 201080059847.7.

(Continued)

*Primary Examiner* — J M Saint Surin
(74) *Attorney, Agent, or Firm* — GE Global Patent Operation

(57) ABSTRACT

An ultrasonic testing method is provided. The ultrasonic method includes non-destructively testing a test object with an ultrasound generated by an ultrasound probe, continuously circulating a liquid coupling medium outside of the test probe before and/or during non-destructively testing the test object, branching a part of the liquid coupling medium off from the circulation, and feeding the branched liquid coupling medium to a coupling chamber arranged between the ultrasound probe and the test object.

16 Claims, 1 Drawing Sheet

(56) References Cited

U.S. PATENT DOCUMENTS

| | | | |
|---|---|---|---|
| 8,443,674 B2 * | 5/2013 | Meinert et al. | 73/649 |
| 8,726,745 B2 * | 5/2014 | Heinze et al. | 73/863.32 |
| 8,813,558 B2 * | 8/2014 | Dockendorff et al. | 73/290 V |
| 2004/1003722 | 6/2004 | Prause | |
| 2005/0154309 A1 * | 7/2005 | Etchells et al. | 600/459 |
| 2006/0055399 A1 | 3/2006 | Georgeson et al. | |

FOREIGN PATENT DOCUMENTS

| | | | |
|---|---|---|---|
| JP | 6079157 U | | 6/1985 |
| JP | 6258103 A | | 3/1987 |
| JP | 0167565 U | | 5/1989 |
| JP | 03245056 A | | 10/1991 |
| JP | 052062 U | | 1/1993 |
| JP | 0680169 U | | 11/1994 |
| JP | 2004138473 A | | 5/2004 |
| JP | 11137909 A | | 5/2009 |
| SU | 827116 | * | 5/1981 |
| SU | 1153946 | * | 5/1985 |

OTHER PUBLICATIONS

Unofficial English translation of Japanese Office Action issued in connection with corresponding JP Application No. 2012-535722 on Aug. 19, 2014, Aug. 11, 1994.

* cited by examiner

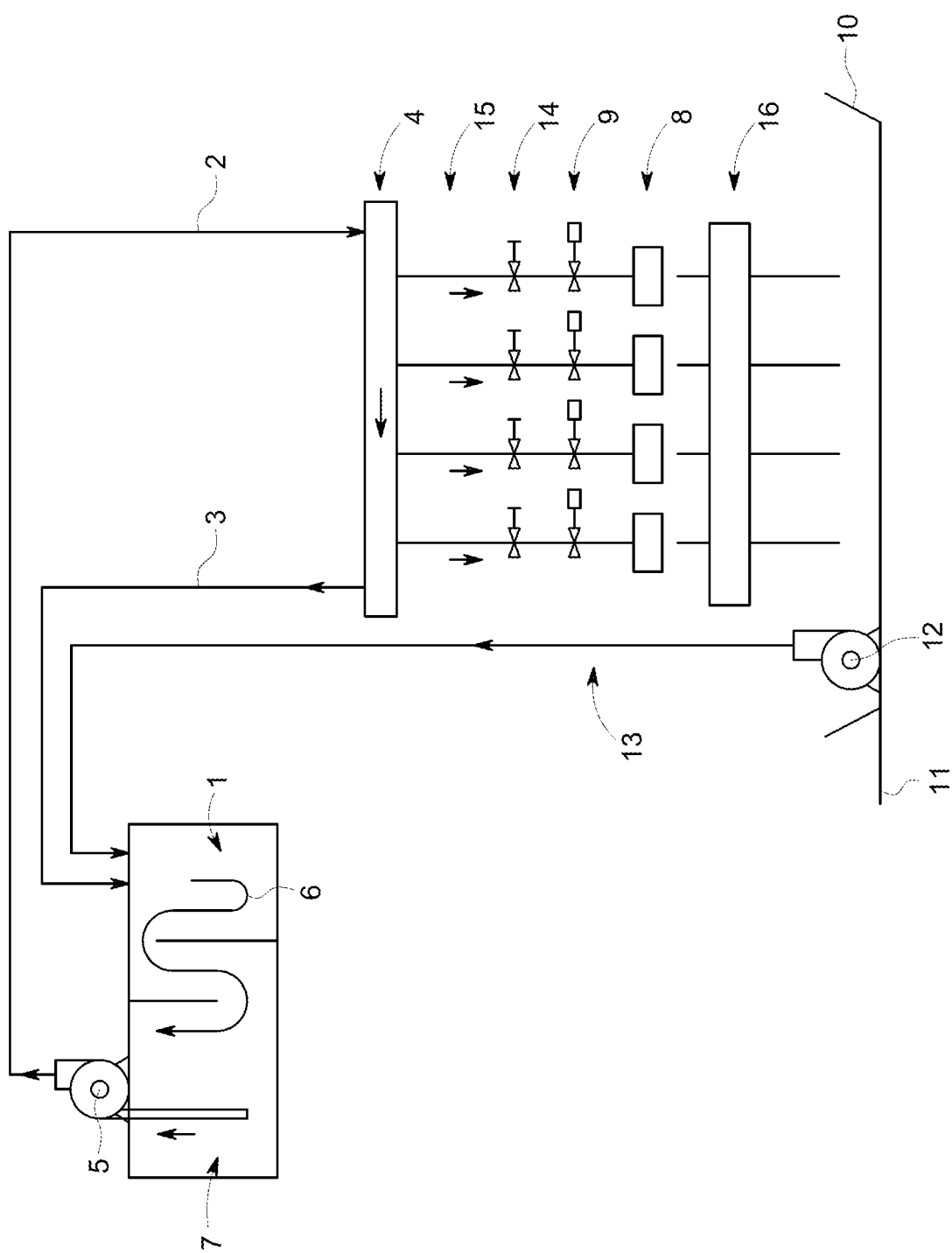

COUPLING MEDIUM SUPPLY OF AN ULTRASONIC TEST DEVICE

CROSS REFERENCE TO RELATED APPLICATIONS

This is a national stage application under 35 U.S.C. §371 (c) of prior-filed, co-pending PCT patent application serial number PCT/EP2010/064712, filed on Oct. 4, 2010, which claims priority to German Patent Application Serial No. 10 2009 051 097.4, filed on Oct. 28, 2009, the entire contents of which are incorporated herein by reference.

BACKGROUND OF THE INVENTION

1. Field of the Invention

Embodiments of the present invention relate to a device and a method for non-destructive ultrasound testing with an improved, in particular more bubble-free, feed of a coupling medium into a coupling chamber between an ultrasound test probe and a test object to be examined in a non-destructive manner by means of ultrasound.

2. Description of the Prior Art

The principle of ultrasonic inspection is known. It serves for finding casting defects or other material faults such as cracks, pockets, piping or the like. The purpose of inspecting bar material is, in particular, the inspection of internal defects and the examination for surface defects, but also the inspection of the dimensions. In this case, the ultrasonic test probe comprises at least one transmitter that is excitable by electrical pulses for generating short ultrasonic pulses that are directed into the material to be inspected of the test object. Any defect in the material to be inspected, for example a crack, a pocket or the like, causes an echo of the pulse concerned, which is reflected back to the probe and is received by the transmitter, which in this case simultaneously serves as a receiver; or the reflected echo can also be received by a separate receiver of the test probe that is disposed adjacent to the transmitter. Measuring the delay in time between the original pulse and the return of the echo permits conclusions to be made with regard to the depth of the defect. The echo strength permits displaying the size of the defect, to mention just this possibility for evaluation as an example. Furthermore, defect determination with spatial resolution is also possible.

A coupling medium is provided for the effective introduction of the emitted ultrasound into the test object. For example, a water area is provided and maintained between the ultrasound test probe and the test object to be inspected, for example the rod. For this purpose, several techniques are known, such as inspection using the immersion technique, the puddle technique or with a guided water jet. Furthermore, sealed water chambers with a test object passage often referred to as SPS also exist. After the test object has entered the sealed water chamber, the test object seals the chamber inlet and outlet. The water chamber is filled with water in order to obtain the coupling between the test probe and the test object.

Furthermore, rotary testing devices are also known. A stable water jacket is generated by rotating the entire inspecting chamber including the test probes. Disposing sealing systems at the inlet and the outlet results in a substantially tubular water jacket through which the test objects can be conveyed.

One difficulty of the known testing systems of this type is that inhomogeneities of the coupling medium, for example, of the water, affect sound propagation which may lead to misinterpretations. In particular, air bubbles in the coupling medium interfere with the inspection.

Therefore, a bubble-free coupling medium is required for ultrasound inspection. This is difficult to ensure, particularly where complex testing systems are concerned that consist of several test probes and test probe holders, and in particular if they are to be switched on or off at different times.

It is particularly difficult to ensure the freedom from bubbles of the coupling medium in such testing systems in which the coupling medium travels over long distances between the water feed and the test probes. The air-bubble-free coupling medium supply is rendered more difficult by the different cross sections and pressure conditions within the supply system, which are unavoidable due to the design requirements, however, because a transition from a rigid pipe to a movable tube, for example, is inevitable.

In the prior art, the freedom from bubbles is accomplished by flow conditions that are as continuous as possible at low flow towards the test flow, by means of large engineering efforts such as regulating valves, bypasses, quick air vents and settling tanks integrated into the supply line. In order to ensure this continuity, even in the case of changing operating conditions, great efforts also have to be made with regard to control engineering; for example, pumps are provided that are controllable by means of frequency converters.

Therefore, embodiment of the present invention provide ultrasound inspection of a test object that is more reliable with regard to diagnosis and simpler with regard to the engineering effort, in particular, of being able to supply a more bubble-free coupling medium.

BRIEF SUMMARY OF THE INVENTION

According to an embodiment of the present invention, an ultrasonic testing method is provided. The ultrasonic method includes non-destructively testing a test object with an ultrasound generated by an ultrasound probe, continuously circulating a liquid coupling medium outside of the test probe before and/or during non-destructively testing the test object, branching a part of the liquid coupling medium off from the circulation, and feeding the branched liquid coupling medium to a coupling chamber arranged between the ultrasound probe and the test object.

According to another embodiment of the present invention, an ultrasonic testing device is provided. The ultrasonic testing device includes an ultrasound test probe configured to generate an ultrasound for non-destructively testing a test object, a coupling chamber arranged between the ultrasound test probe and the test object, a circulation circuit configured to continuously circulate a liquid coupling medium outside of the ultrasound test probe before and/or during non-destructively testing the test object, and a branch fluidly connecting the circulation circuit to the coupling chamber, through which the liquid coupling medium is fed to the coupling chamber.

BRIEF DESCRIPTION OF THE DRAWINGS

Embodiments of the present invention, as well as the technical environment, are explained below in more detail with reference to the FIGURE. It must be remarked that the FIGURE depicts a particularly preferred embodiment of the invention, but that it is not limited thereto. The FIGURE schematically shows FIG. 1 is a schematic view for carrying out the method according to an embodiment of the invention.

DETAILED DESCRIPTION OF THE INVENTION

Embodiments of the present invention provide a method according to claim 1 and a device of the independent claim. It must be remarked that the features cited individually in the patent claims can be combined in any technologically meaningful manner and depict other embodiments of the invention. The description, in particular in connection with the figures, additionally characterizes and specifies the invention.

The ultrasound testing method provides that a test object is non-destructively inspected in an ultrasound testing step by means of ultrasound generated by an ultrasound test probe. The invention is not limited with regard to the technology used in the ultrasound testing or with regard to the test object. In principle, the method is suitable for any type of ultrasound inspection in which a liquid, and thus flowable coupling medium, is provided for acoustic coupling between the test probe and the test object. The test object may therefore be, for example, a living organism, an item consisting of metal or plastic, a hollow or a massive item.

It is provided, according to embodiments of the present invention, that the coupling medium is brought into a continuous circulation outside of the test probe. The term continuous circulation is to be interpreted broadly and provides that the medium is to be conducted in a circuit, for example through pipes. According to the invention, the flow speed does not have to be kept constant in the process. Continuous within the sense of embodiments of the present invention provides that the flow is not interrupted, i.e. that the flow speed is not reduced to zero.

According to embodiments of the present invention, a part is branched off from the circulation, i.e. the circulating coupling medium, and this part is fed to a coupling chamber between the ultrasound test probe and the test object. Due to the fact that the coupling medium is only partially conducted via the ultrasound test probe and is conducted in a circuit outside the ultrasound test probe before and/or during the ultrasound testing, the coupling medium can be efficiently settled and/or degassed in the circulation in order to only then be fed to the ultrasound test probe. The freedom from bubbles of the coupling medium is thus improved and the quality of the ultrasound diagnostics increased.

In an embodiment of the method according to the invention, a feed is furthermore provided for compensating for the loss of coupling medium.

In an embodiment, the circulation routing is provided outside of and distant from the device carrying the test probe. In the case of the circulation routing outside of the device carrying the test probe, the pipes conducting the coupling medium can thus be shortened as compared with a circulation in the vicinity of the test probe because, for example, only a branch pipe to the test probe is provided.

Another substantial advantage of a circulation outside of the test probe is the fact that the inflow of the coupling medium towards the test probe can be controlled by means for interrupting the feed, such as a valve, without interrupting the circulation, i.e. that the coupling medium supply for the test probe can be switched on and off without air bubbles forming in the entire supply system due to the above-mentioned changes to the pressure and flow conditions. In an embodiment of the present invention, the branch-off of the coupling medium from the circulation is interrupted at least before and after the ultrasound testing step without interrupting the circulation.

According to an embodiment of the present invention, the coupling medium is returned to the circulation after having been supplied to the coupling chamber. The coupling medium consumption can thus be reduced.

In an embodiment of the present invention, the coupling medium is continuously branched off from the circulation and continuously supplied to the test object during the ultrasound testing step. By avoiding interruptions in the coupling medium flow, and by avoiding pressure fluctuations associated therewith, in particular pressure drops when the supply line is reopened, air bubble formation is minimized.

In an embodiment of the present invention, the coupling medium substantially comprises water, among other things for cost-related reasons. In another embodiment of the present invention, the coupling medium is natural water.

In an embodiment of the present invention, the coupling medium is degassed in the circulation. Degassing within the sense means that means for degassing are provided that promote the degassing of the flowing coupling medium. In an embodiment of the present invention, this is a settling tank. The feed provided according to an embodiment for compensating for the loss of coupling medium takes place in the settling tank. According to another embodiment, the means for degassing are configured in such a way that a meandering routing or flow of the coupling medium is obtained. The changes of the flow direction achieved thereby are conducive to the degassing of the coupling medium. In an embodiment of the present invention, the meandering flow routing is integrated into the settling tank.

According to another embodiment of the present invention, the means for degassing are configured in such a way that a flow of the coupling medium is obtained which follows the direction of gravity. If the coupling medium flows following gravity, the separation of the air bubbles and the coupling medium, and thus degassing, is facilitated. This flow direction can be realized by vertical flow paths in the meandering routing in the settling tank.

The method according to embodiments of the present invention is suitable particularly in the case of such methods in which the test object, during the ultrasound testing step or intermittently between several ultrasound testing steps, is moved relative to the test probe or vice versa.

The method described herein has proved to be particularly advantageous in the testing devices described in the published patent specifications DE 19931350 A1 and DE 10 2007 039 325 A1, which are hereby incorporated by reference in this regard.

The freedom from bubbles of the coupling medium has proved to be particularly advantageous in the case of such test objects in which the ultrasound cannot be coupled in into a plane surface. Therefore, the method according to the invention may be used in a rod or pipe as a test object.

Embodiments of the present invention further relate to an ultrasound testing device, wherein the advantages mentioned above with regard to the specific embodiment of the method also pertain to the respective device.

The device according to the embodiments of the present invention comprises the following: an ultrasound test probe for carrying out an ultrasound testing step on a test object by means of ultrasound generated by the ultrasound test probe, means for feeding a liquid coupling medium into a coupling chamber between the ultrasound test probe and the test object. The device is characterized in that means for bringing the coupling medium into a continuous circulation outside of the test probe, and even outside of the device carrying the test probe, and means for branching off a part of the coupling medium from the circulation for the feed into the coupling chamber, are provided.

Due to the fact that the coupling medium is only partially fed via or to the ultrasound test probe, and is conducted in a circuit outside the ultrasound test probe before and/or during the ultrasound testing, the coupling medium can be efficiently settled and/or degassed in the circulation in order to only then be efficiently fed to the ultrasound test probe in a degassed state, for example in a branch pipe. The freedom from bubbles of the coupling medium is thus improved and the quality of the ultrasound diagnostics of the ultrasound device is increased over the prior art. Moreover, the pipes conducting the coupling medium can be shortened in the case of a circulation routing outside of the test probe. Another substantial advantage of a circulation outside of the test probe is the fact that the inflow of the coupling medium towards the test probe can be controlled without interrupting the circulation, i.e. that the coupling medium supply for the test probe can be switched on and off without interrupting the degassing in the circulation, avoiding the problem of air bubbles forming in the entire supply system due to the above-mentioned changes to the pressure and flow conditions. Therefore, means for interrupting the feed of the coupling medium into the coupling chamber, such as a valve or the like, may be provided that do not interrupt circulation because they are provided, for example, in the feed pipe to the test probe.

In order to reduce the loss of coupling medium, means for returning into the circulation the coupling medium fed to the coupling chamber, such as collecting systems, may be provided.

As was described above, means for degassing the coupling medium are may be provided.

FIG. 1 schematically shows the method according to an embodiment of the present invention, with substantially only the components provided for the coupling medium supply being shown, and, with the exception of the test probes, the components provided for the ultrasound inspection and the test object concerned not being shown for the sake of clarity. The coupling medium, which may be natural water, serves for the acoustic coupling between the respective test probe 8 and the test object to be inspected by means of ultrasound, and for this purpose, it is fed to a coupling chamber 16 provided therefore. The coupling medium supply according to embodiments of the present invention provides a continuous circulation of the coupling medium. The circulation process can be carried out during and/or before the ultrasound testing. The forced circulation in the embodiment shown is realized by the pipes 2, 3 and the distributor 4, the settling tank 1 and the pump 5. In this case, the settling tank 1 and in particular the meandering pipe system 6 provided therein are provided for degassing the coupling medium. This meandering pipe system 6 is routed in such a way that partial sections that are as long as possible are provided in which the course of the flow is selected in such a way that the coupling medium flows following its direction of gravity, which is conducive to the separation of air bubbles and the medium, and thus, to degassing. An area 7 is moreover provided in the settling tank 1 which serves for feeding new coupling medium in order to be able to compensate for the loss of coupling medium.

A part of the coupling medium is branched off from the circulation through the distributor 4 and is fed to the test probes 8 via branch pipes 15 that can be shut off by manually operated shut-off valves 14 and pneumatically operated valves 9. The coupling medium escaping the coupling chamber is collected by a collecting trough and returned to circulation, i.e. the settling tank 1, by means of the pump 12 and the return pipe 13. An outlet 11 is provided for the maintenance, cleaning and the like of the system. Due to the fact that the coupling medium is only partially conducted via the ultrasound test probe and is conducted in a circuit before and/or during the ultrasound testing, the coupling medium can be efficiently settled and/or degassed in the circulation in order to only then be fed to the ultrasound test probe. The freedom from bubbles of the coupling medium is thus improved and the quality of the ultrasound diagnostics increased. Moreover, by means of the circulation routing according to embodiments of the present invention in which the test probe is not integrated into the circulation provided for degassing, the pipes conducting the coupling medium can be shortened as compared with a circulation only via the test probe. Another substantial advantage of a circulation outside of the test probe is the fact that the inflow of the coupling medium towards the test probe can be controlled, i.e. that the coupling medium supply for the test probe can be switched on and off without air bubbles forming in the entire supply system due to the above-mentioned changes to the pressure and flow conditions.

The invention claimed is:

1. An ultrasonic testing method comprising:
   non-destructively testing a test object with an ultrasound generated by an ultrasound probe, a coupling chamber arranged between the ultrasound probe and the test object;
   continuously circulating a liquid coupling medium outside of the coupling chamber before and/or during non-destructively testing the test object;
   branching a part of the liquid coupling medium off from the circulation; and
   feeding the branched liquid coupling medium to the coupling chamber.

2. The method according to claim 1 further comprising returning the coupling medium to the circulation after the coupling medium has been fed to the coupling chamber.

3. The method according to claim 1, wherein the part of the liquid coupling medium is continuously branched off from the circulation and the branched liquid coupling medium is continuously fed to the coupling chamber during the non-destructive testing the test object.

4. The method according to claim 1, wherein branching the part of the liquid coupling medium off from the circulation is interrupted at least before and after the non-destructive testing the test object without interrupting the continuous circulation of the liquid coupling medium.

5. The method according to claim 1, wherein the liquid coupling medium comprises water.

6. The method according to claim 1, wherein the liquid coupling medium comprises natural water.

7. The method according to claim 1, wherein the liquid coupling medium is degassed in the circulation.

8. The method according to claim 1, wherein the test object is moved relative to the ultrasound probe, or the ultrasound probe is moved relative to the test object, during the non-destructive testing the test object.

9. The method according to claim 1, wherein the test object is a bar or a tube.

10. An ultrasonic testing device comprising:
    an ultrasound test probe configured to generate an ultrasound for non-destructively testing a test object;
    a coupling chamber arranged between the ultrasound test probe and the test object;
    a circulation circuit configured to continuously circulate a liquid coupling medium outside of the coupling chamber before and/or during non-destructively testing the test object; and
    a branch fluidly connecting the circulation circuit to the coupling chamber through which the liquid coupling medium is fed to the coupling chamber.

11. The ultrasonic testing device of claim 10, further comprising a pump configured to return the liquid coupling medium to the circulation circuit.

12. The ultrasonic testing device of claim 10, further comprising valves configured to interrupt flow of the liquid coupling medium to the coupling chamber without interrupting continuous circulation of the liquid coupling medium in the circulation circuit.

13. The ultrasonic testing device of claim 10, wherein the circulation circuit comprises a settling tank configured to degas the liquid coupling medium.

14. The ultrasonic testing device of claim 13, wherein the settling tank comprises meandering routing of the liquid coupling medium.

15. The ultrasonic testing device of claim 13, wherein flow of the liquid coupling medium in the settling tank follows the direction of gravity.

16. The ultrasonic testing device of claim 10, wherein the test object is moved relative to the ultrasound probe, or the ultrasound probe is moved relative to the test object, during the non-destructive testing the test object.

* * * * *